(12) United States Patent
Wax et al.

(10) Patent No.: US 8,537,366 B2
(45) Date of Patent: *Sep. 17, 2013

(54) SYSTEMS AND METHODS FOR ENDOSCOPIC ANGLE-RESOLVED LOW COHERENCE INTERFEROMETRY

(75) Inventors: Adam Wax, Chapel Hill, NC (US); John W. Pyhtila, Durham, NC (US)

(73) Assignee: Duke University, Durham, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 13/042,672

(22) Filed: Mar. 8, 2011

(65) Prior Publication Data

US 2011/0157596 A1  Jun. 30, 2011

Related U.S. Application Data

(63) Continuation of application No. 12/538,309, filed on Aug. 10, 2009, now Pat. No. 7,903,254, which is a continuation of application No. 11/548,468, filed on Oct. 11, 2006, now Pat. No. 7,595,889.

(60) Provisional application No. 60/725,403, filed on Oct. 11, 2005.

(51) Int. Cl.
G01B 9/02 (2006.01)
G01J 3/45 (2006.01)

(52) U.S. Cl.
USPC .......................................................... 356/456

(58) Field of Classification Search
USPC .................................. 356/451, 456, 477, 479
See application file for complete search history.

(56) References Cited

U.S. PATENT DOCUMENTS 2,469,906 A  5/1949  Wallace
4,646,722 A  3/1987  Silverstein et al.
(Continued)

FOREIGN PATENT DOCUMENTS

CN  12836086 A  2/2001
EP  0243005 A2  10/1987
(Continued)

OTHER PUBLICATIONS

Xie, Tuqiang et al., "Fiber-Optic-Bundle-Based Optical Coherehence Tomography," Optic Letters, vol. 30, No. 14, Jul. 15, 2005.

(Continued)

Primary Examiner — Michael A Lyons
(74) Attorney, Agent, or Firm — Michael G. Johnston; Moore & Van Allen PLLC

(57) ABSTRACT

Fourier domain a/LCI (faLCI) system and method which enables in vivo data acquisition at rapid rates using a single scan. Angle-resolved and depth-resolved spectra information is obtained with one scan. The reference arm can remain fixed with respect to the sample due to only one scan required. A reference signal and a reflected sample signal are cross-correlated and dispersed at a multitude of reflected angles off of the sample, thereby representing reflections from a multitude of points on the sample at the same time in parallel. Information about all depths of the sample at each of the multitude of different points on the sample can be obtained with one scan on the order of approximately 40 milliseconds. From the spatial, cross-correlated reference signal, structural (size) information can also be obtained using techniques that allow size information of scatterers to be obtained from angle-resolved data.

66 Claims, 8 Drawing Sheets

(56) References Cited

U.S. PATENT DOCUMENTS

| | | | |
|---|---|---|---|
| 4,741,326 A | 5/1988 | Sidall et al. | |
| 5,184,602 A | 2/1993 | Anapliotis et al. | |
| 5,193,525 A | 3/1993 | Silverstein et al. | |
| 5,386,817 A | 2/1995 | Jones | |
| 5,489,256 A | 2/1996 | Adair | |
| 5,534,707 A | 7/1996 | Pentoney | |
| 5,565,986 A | 10/1996 | Knuttel | |
| 5,601,087 A | 2/1997 | Gunderson et al. | |
| 5,643,175 A | 7/1997 | Adair | |
| 5,771,327 A | 6/1998 | Bar-Or et al. | |
| 5,930,440 A | 7/1999 | Bar-Or | |
| 5,956,355 A * | 9/1999 | Swanson et al. | 372/20 |
| 6,002,480 A * | 12/1999 | Izatt et al. | 356/479 |
| 6,091,984 A * | 7/2000 | Perelman et al. | 600/476 |
| 6,134,003 A * | 10/2000 | Tearney et al. | 356/479 |
| 6,174,291 B1 | 1/2001 | McMahon et al. | |
| 6,233,373 B1 | 5/2001 | Askins et al. | |
| 6,263,133 B1 | 7/2001 | Hamm | |
| 6,404,497 B1 * | 6/2002 | Backman et al. | 356/369 |
| 6,447,444 B1 | 9/2002 | Avni et al. | |
| 6,501,551 B1 | 12/2002 | Tearney et al. | |
| 6,564,087 B1 | 5/2003 | Pitris et al. | |
| 6,624,890 B2 | 9/2003 | Backman et al. | |
| 6,697,652 B2 | 2/2004 | Georgakoudi et al. | |
| 6,775,007 B2 * | 8/2004 | Izatt et al. | 356/497 |
| 6,847,456 B2 | 1/2005 | Yang et al. | |
| 6,853,457 B2 | 2/2005 | Bjarklev et al. | |
| 6,855,107 B2 | 2/2005 | Avni et al. | |
| 6,863,651 B2 | 3/2005 | Remijan et al. | |
| 6,879,741 B2 | 4/2005 | Salerno et al. | |
| 7,061,622 B2 | 6/2006 | Rollins et al. | |
| 7,079,254 B2 | 7/2006 | Kane et al. | |
| 7,102,758 B2 | 9/2006 | Wax | |
| 7,190,464 B2 | 3/2007 | Alphonse | |
| 7,355,716 B2 | 4/2008 | de Boer et al. | |
| 7,366,372 B2 | 4/2008 | Lange | |
| 7,391,520 B2 | 6/2008 | Zhou et al. | |
| 7,408,052 B2 | 8/2008 | Cheikh et al. | |
| 7,417,740 B2 | 8/2008 | Alphonse et al. | |
| 7,428,050 B2 | 9/2008 | Giakos | |
| 7,428,052 B2 * | 9/2008 | Fujita | 356/479 |
| 7,595,889 B2 * | 9/2009 | Wax et al. | 356/456 |
| 7,616,323 B2 * | 11/2009 | De Lega et al. | 356/511 |
| 7,633,627 B2 * | 12/2009 | Choma et al. | 356/479 |
| 7,636,168 B2 * | 12/2009 | De Lega et al. | 356/512 |
| 7,761,139 B2 | 7/2010 | Tearney et al. | |
| 7,884,947 B2 * | 2/2011 | De Lega et al. | 356/511 |
| 7,903,254 B2 * | 3/2011 | Wax et al. | 356/456 |
| 2002/0143243 A1 | 10/2002 | Georgakoudi et al. | |
| 2002/0171831 A1 | 11/2002 | Backman et al. | |
| 2002/0188204 A1 | 12/2002 | McNamara et al. | |
| 2003/0042438 A1 | 3/2003 | Lawandy et al. | |
| 2003/0137669 A1 | 7/2003 | Rollins et al. | |
| 2003/0153866 A1 | 8/2003 | Long et al. | |
| 2003/0187349 A1 | 10/2003 | Kaneko et al. | |
| 2004/0215296 A1 | 10/2004 | Ganz et al. | |
| 2004/0223162 A1 | 11/2004 | Wax | |
| 2005/0000525 A1 | 1/2005 | Klimberg et al. | |
| 2005/0004453 A1 | 1/2005 | Tearney et al. | |
| 2005/0053974 A1 | 3/2005 | Lakowicz et al. | |
| 2005/0182291 A1 | 8/2005 | Hirata | |
| 2006/0132790 A1 | 6/2006 | Gutin | |
| 2006/0158657 A1 * | 7/2006 | De Lega et al. | 356/497 |
| 2006/0158659 A1 * | 7/2006 | Colonna De Lega et al. | 356/497 |
| 2006/0164643 A1 | 7/2006 | Giakos | |
| 2006/0241577 A1 | 10/2006 | Balbierz et al. | |
| 2006/0256343 A1 | 11/2006 | Choma et al. | |
| 2006/0285635 A1 | 12/2006 | Boppart et al. | |
| 2007/0002327 A1 | 1/2007 | Zhou et al. | |
| 2007/0015969 A1 * | 1/2007 | Feldman et al. | 600/160 |
| 2007/0027391 A1 | 2/2007 | Kohno | |
| 2007/0086013 A1 | 4/2007 | De Lega et al. | |
| 2007/0091318 A1 * | 4/2007 | Freishlad et al. | 356/511 |
| 2007/0133002 A1 | 6/2007 | Wax et al. | |
| 2007/0139656 A1 * | 6/2007 | Wan | 356/504 |
| 2007/0165234 A1 * | 7/2007 | Podoleanu | 356/451 |
| 2007/0201033 A1 * | 8/2007 | Desjardins et al. | 356/497 |
| 2007/0270792 A1 | 11/2007 | Hennemann et al. | |
| 2008/0037024 A1 | 2/2008 | Backman et al. | |
| 2008/0058629 A1 | 3/2008 | Seibel et al. | |
| 2008/0174784 A1 * | 7/2008 | Colonna De Lega et al. | 356/511 |
| 2008/0249369 A1 | 10/2008 | Seibel et al. | |
| 2008/0255461 A1 | 10/2008 | Weersink et al. | |
| 2009/0009759 A1 | 1/2009 | Backman et al. | |
| 2009/0073456 A1 * | 3/2009 | Wax et al. | 356/479 |
| 2009/0075391 A1 | 3/2009 | Fulghum, Jr. | |

FOREIGN PATENT DOCUMENTS

| | | |
|---|---|---|
| EP | 1021126 B1 | 7/2004 |
| JP | 61210910 A | 9/1986 |
| WO | 9918845 | 4/1999 |
| WO | 0042912 A1 | 7/2000 |
| WO | 2007133684 A2 | 11/2007 |

OTHER PUBLICATIONS

Pyhtila, John W. et al., "Fourier-Domain Angle-Resolved Low Coherence Interferometry Through an Endoscopic Fiber Bundle for Light-Scattering Spectroscopy," Optics Letters, vol. 31, No. 6, Mar. 15, 2006.

Pyhtila, John W. et al., "Rapid, Depth-Resolved Light Scattering Measurements using Fourier Domain, Angle-Resolved Low Coherence Interferometry," Optics Express, vol. 12, No. 25, Dec. 13, 2004.

Pyhtila, John W. et al., "Determining Nuclear Morphology Using an Improved Angle-Resolved Low Coherence Interferometry System," Optics Express, vol. 11, No. 25, Dec. 15, 2003.

Hausler, G. et al., "Coherence Radar and Spectral Radar—New Tools for Dermatological Diagnosis," Journal of Biomedical Optics, vol. 3, Jan. 1998.

Wax, Adam et al., "Cellular Organization and Substructure Measured Using Angle-Resolved Low-Coherence Interferometry," Biophysical Journal, Apr. 2002, pp. 2256-2264, vol. 82.

Pyhtila, John W. et al., "Experimental Calibration of a New Angle-Resolved Low Coherence Interferometry System," http://www.fitzpatrick.duke.edu/Events/AnnualMeetings/04.ThePhysicalNatureofInformation/posters/htm, 2003.

Wax, Adam et al., "Measurement of Angular Distributions by Use of Low-Coherence Interferometry for Light-Scattering Spectroscopy," Optics Letters, Mar. 15, 2001, pp. 322-324, vol. 26, No. 6.

Wax, Adam et al., "Determination of Particle Size Using the Angular Distribtion of Backscattered Light as Measured with Low-Coherence Interferometry," Journal of the Optical Society of America, Apr. 2002, pp. 737-744, vol. 19, No. 4.

Wax, Adam et al., "In Situ Detection of Neoplastic Transformation and Chemopreventive Effects in Rat Esophagus Epithelium Using Angle-Resolved Low-Coherence Interferometry," Cancer Research, Jul. 1, 2003, pp. 3556-3559, vol. 63, No. 13.

Leitgeb, R. et al., "Performance of Fourier Domain vs. Time Domain Optical Coherence Tomography," Optics Express, vol. 11, No. 8, Apr. 21, 2003, pp. 889-894.

de Boer, Johannes F. et al., "Improved Signal-To-Noise Ratio in Spectral-Domain Compared with Time-Domain Optical Coherence Tomography," Optics Letters, vol. 28, No. 21, Nov. 1, 2003, pp. 2067-2069, http://oa.osa.org/abstract.cfm?id=86605.

Choma, Michael A. et al., "Sensitivity Advantage of Swept Source and Fourier Domain Optical Coherence Tomography," Optics Express, vol. 11, No. 18, Sep. 8, 2003, pp. 2183-2189.

Kim, Y.L. et al., "Simultaneous Measurement of Angular and Spectral Properties of Light Scattering for Characterization of Tissue Microarchitecture and its Alteration in Early Precancer," IEEE Journal of Selected Topics in Quantum Electronics, vol. 9, Issue 2, Mar./Apr. 2003, pp. 243-256, http://ieeexplore.ieee.org/xpl/freeabs_all.jsp?tp=&arnumber=1238988&isnumber=27791.

Roy, Hemant K. et al., "Four-Dimensional Elastic Light-Scattering Fingerprints as Preneoplastic Markers in the Rat Model of Colon Carcinogenesis," Gastroenterology, vol. 126, Issue 4, Apr. 2004, pp. 1071-1081, http://www.gastrojournal.org/article/PIIS0016508501000290/abstract.

Wax, Adam et al., "In Situ Monitoring of Neoplastic Transformation and Assessing Efficacy of Chemopreventive Agents in Rat Esophagus Epithelium Using Angle-Resolved Low-Coherence Interferometry," Abstract as presented to the American Association for Cancer Research at their 2004 Annual Meeting, Mar. 27, 2004.

Wax, Adam et al., "Prospective Grading of Neoplastic Change in Rat Esophagus Epithelium Using Angle-Resolved Low-Coherence Interferometry," Journal of Biomedical Optics, vol. 10(5), Sep./Oct. 2005, pp. 051604-1 through 051604-10.

Brown, William J. et al., "Review and Recent Development of Angle-Resolved Low-Coherence Interferometry for Detection of Precancerous Cells in Human Esophageal Epithelium," IEEE Journal of Selected Topics in Quantum Electronics, vol. 14, No. 1, Jan./Feb. 2008, pp. 88-97.

Wax, Adam et al., "Fourier-Domain Low-Coherence Interferometry for Light-Scattering Spectroscopy," Optic Letters, vol. 28, No. 14, Jul. 15, 2003, pp. 1230-1232.

Backman, V. et al., "Measuring Cellular Structure at Submicrometer Scale with Light Scattering Spectroscopy," IEEE J. Sel. Top. Quantum Electron, vol. 7, Issue 6, Nov./Dec. 2001, pp. 887-893.

Backman, V. et al., "Detection of Preinvasive Cancer Cells," Nature 406, Jul. 6, 2000, pp. 35-36.

Wojtkowski, M. et al., "Full Range Complex Spectral Optical Coherence Tomography Technique in Eye Imaging," Optics Letters, vol. 27, Issue 16, Aug. 15, 2002, pp. 1415-1417.

Wojtkowski, M. et al., "In Vivo Human Retinal Imaging by Fourier Domain Optical Coherence Tomography," J. Biomed. Opt., vol. 7, No. 3, Jul. 1, 2002, pp. 457-463.

Leitgeb, R. et al., "Spectral Measurement of Absorption by Spectroscopic Frequency-Domain Optical Coherence Tomography," Optic Letters, vol. 25, Issue 11, Jun. 1, 2000, pp. 820-822.

Morgner, U. et al., "Spectroscopic Optical Coherence Tomography," Optic Letters, vol. 25, Issue 2, Jan. 15, 2000, pp. 111-113.

Tuchin, V. et al., Tissue Optics: Light Scattering Methods and Instruments for Medical Diagnosis, SPIE, May 2000.

Amoozegar, Cyrus et a., "Experimental Verification of T-matrix-based Inverse Light Scattering Analysis for Assessing Structure of Spheroids as Models of Cell Nuclei," Applied Optics, vol. 48, No. 10, Apr. 1, 2009, 7 pages.

Graf, R. N. et al., "Parallel Frequency-Domain Optical Coherence Tomography Scatter-Mode Imaging of the Hamster Cheek Pouch Using a Thermal Light Source," Optics Letters, vol. 33, No. 12, Jun. 15, 2008, pp. 1285-1287.

Robles, Francisco et al., "Dual Window Method for Processing Spectroscopic OCT Signals with Simultaneous High Spectral and Temporal Resolution," Optical Society of America, 2008, 12 pages.

Keener, Justin D. et al., "Application of Mie Theory to Determine the Structure of Spheroidal Scatterers in Biological Materials," Optics Letters, vol. 32, No. 10, May 15, 2007, pp. 1326-1328.

Chalut, Kevin J. et al., "Application of Mie Theory to Assess Structure of Spheroidal Scattering in Backscattering Geometries," J. Opt. Soc. Am. A, vol. 25, No. 8, Aug. 2008, pp. 1866-1874.

Chalut, Kevin J. et al., "Light Scattering Measurements of Subcellular Structure Provide Noninvasive Early Detection of Chemotherapy-induced Apoptosis," not yet published, 2009, 25 pages.

Chalut, Kevin J., et al., "Label-Free, High-Throughput Measurements of Dynamic Changes in Cell Nuclei Using Angle-Resolved Low Coherence Interferometry," Biophysical Journal, vol. 94, Jun. 2008, pp. 4948-4956.

Giacomelli, Michael G. et al., "Application of the T-matrix Method to Determine the Structure of Spheroidal Cell Nuclei with Angle-resolved Light Scattering," Optics Letters, vol. 33, No. 21, Nov. 1, 2008, pp. 2452-2454.

Wax, Adam, "Proposed Research Plan," Case Western Reserve University, Biomedical Engineering Department, last modified on Feb. 1, 2002—Submitted As Proprietary Document.

Wax, Adam, "Studying the Living Cell Using Light Scattering and Low-Coherence Interferometry," Laser Biomedical Research Center, MIT Spectroscopy Laboratory, presented at Case Western Reserve University 2002, Feb. 1, 2002.

Pyhtila, John W. et al., "Polarization Effects on Scatterer Sizing Accuracy Analyzed with Frequency-Domain Angle-Resolved Low-Coherence Interferometry," Applied Optics, vol. 46, No. 10, Apr. 1, 2007.

Pyhtila, John W. et al., "Coherent Light Scattering by in Vitro Cell Arrays Observed with Angle-Resolved Low Coherence Interferometry," SPIE, vol. 5690, 2005.

Wax, Adam et al., "Angular Light Scattering Studies Using Low-Coherence Interferometry," SPIE, vol. 4251, 2001.

Grant Progress Report for "In Vivo Detection of Pre-Cancerous Lesions Using a/LCI", Dec. 2005, pp. 1-9.

Wax, Adam, Proposal submitted to National Institutes of Health for "In Vivo Detection of Pre-Cancerous Lesions Using a/LCI," Nov. 19, 2003, pp. 1-64.

Wax, Adam, "In Vivo Detection of Pre-Cancerous Lesions Using a/LCI," Abstract, printed from Computer Retrieval of Information on Scientific Projects (CRISP), Aug. 1, 2004, 2 pages.

Wax, Adam, "Coherence and Spectroscopy Studies for Biomed Imaging," Abstract, printed from http://www.researchgrantdatabase.com, 2000, 1 page.

Wax, Adam, "Assessing Nuclear Morphology in Thick Tissues Using FLCI," Abstract, printed from http://www.researchgrantdatabase.com, Apr. 14, 2006, 1 page.

Wax, Adam, "Assessing Deployment of Microbicidal Gels with Label-Free Optical Measurement," Abstract, printed from http://www.researchgrantdatabase.com, Jul. 1, 2007, 2 pages.

Wax, Adam, "In Vivo Detection of Pre-Cancerous Lesions Using a/LCI," Abstract, printed from http://www.researchgrantdatabase.com, Aug. 1, 2004, 1 page.

Wax, Adam et al., "Angle-Resolved Low Coherence Interferometry for Detection of Dysplasia in Barrett's Esophagus," Gastroenterology, vol. 141, No. 2, Aug. 2011, pp. 443-447.

Wax, Adam et al., "Nuclear morphology measurements with angle-resolved low coherence interferometry for application to cell biology and early cancer detection," Analytical Cellular Pathology 1, published Aug. 12, 2011, 16 pages.

Zhu, Yizheng et al., "Development of angle-resolved low coherence interferometry for clinical detection of dysplasia," Journal of Carcinogenesis, vol. 10, Issue 1, published Aug. 23, 2011, p. 19, 9 pages.

Bouma, Brett Eugene, Declaration Under 37 C.F.R. 1.131 filed in U.S. Appl. No. 11/677,278, Feb. 1, 2010.

Wax, Adam, Real-time a/LCI measurements for detecting pre-cancerous cells, Optical Society of America FiO and Laser Science Frontiers in Optics 2004 and Laser Science XX, Oct. 10-14, 2004.

Pyhtila, J., et al., Real-time data acquisition angle-resolved low coherence interferometry system, Biomedical Engineering Society, 2004 BMES Annual Fall Meeting, Biomedical Engineering: New Challenges for the Future, Oct. 13-16, 2004.

Duke University, European Patent Application No. 11176357.9, Extended European Search Report, Mar. 23, 2012.

Duke University, Australian Patent Application No. 2011244958, Examination Report No. 1, Aug. 3, 2012.

Duke University, Indian Appl. No. 649/MUMNP/2008, First Examination Report, Nov. 29, 2012.

Vabre, L, et al., Imagery of local defects in multilayer components by short coherence length interferometry, Optics Letters, pp. 1899-1901, Nov. 1, 2002, vol. 27, No. 21.

Tuchin, V., Tissue Optics: Light Scattering Methods and Instruments for Medical Diagnosis, 2000, pp. 40-44, 91-98.

Duke University, Japanese Application No. 2008-535655, Office Action, Oct. 16, 2012.

Duke University, Japanese Application No. 2012-106902, Notice of Rejection, May 7, 2013.

* cited by examiner

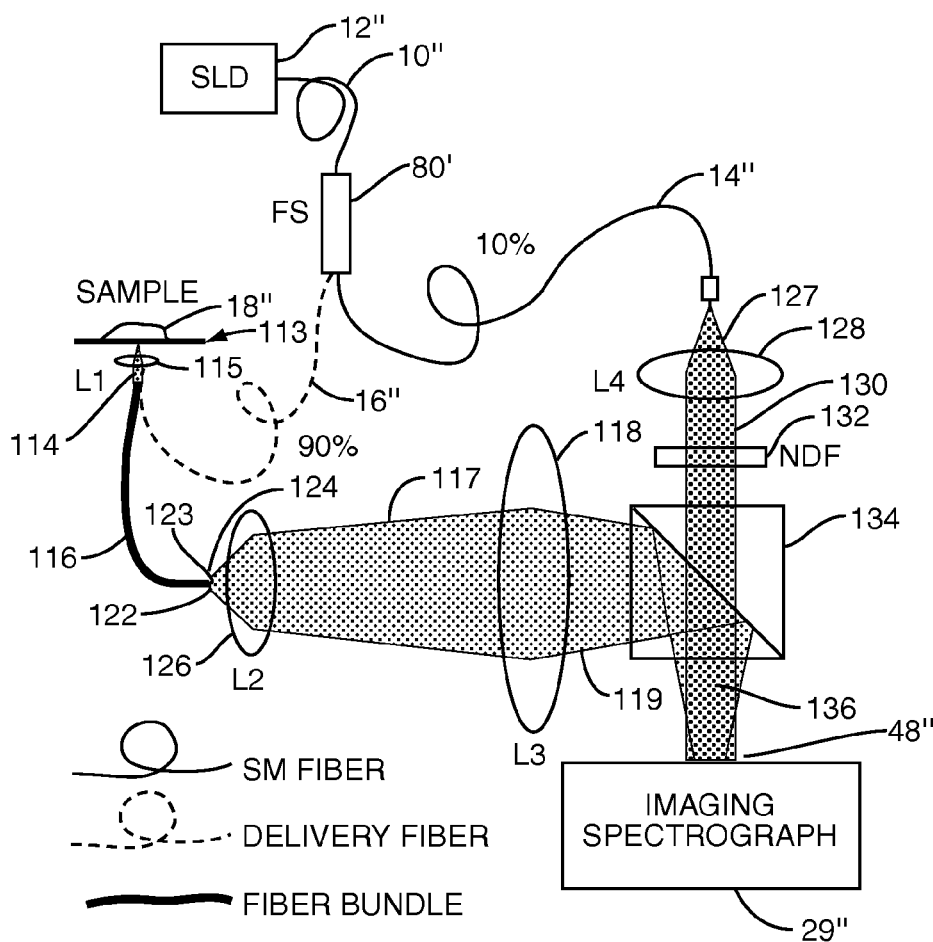
FIG. 8A
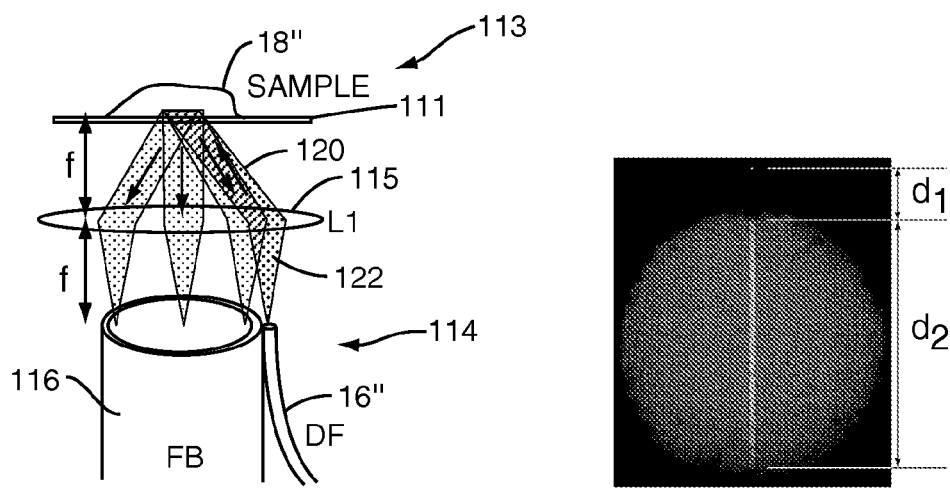
FIG. 8B  FIG. 8C

SYSTEMS AND METHODS FOR ENDOSCOPIC ANGLE-RESOLVED LOW COHERENCE INTERFEROMETRY

RELATED APPLICATIONS

This application is a continuation application of U.S. patent application Ser. No. 12/538,309 entitled "SYSTEMS AND METHODS FOR ENDOSCOPIC ANGLE-RESOLVED LOW COHERENCE INTERFEROMETRY," filed on Aug. 10, 2009, which is herein incorporated by reference in its entirety and which is a continuation application of U.S. patent application Ser. No. 11,548,648, now U.S. Pat. No. 7,595,889, entitled "SYSTEMS AND METHODS FOR ENDOSCOPIC ANGLE-RESOLVED LOW COHERENCE INTERFEROMETRY," filed on Oct. 11, 2006, which is herein incorporated by reference in its entirety, which claims priority to U.S. Provisional Patent Application No. 60/725,603 entitled "SYSTEMS AND METHODS FOR ENDOSCOPIC ANGLE-RESOLVED LOW COHERENCE INTERFEROMETRY," filed on Oct. 11, 2005, also incorporated herein by reference in its entirety.

This application is also related to U.S. Pat. No. 7,102,758 entitled "FOURIER DOMAIN LOW-COHERENCE INTERFEROMETRY FOR LIGHT SCATTERING SPECTROSCOPY APPARATUS AND METHOD," which is incorporated herein by reference in its entirety.

STATEMENT REGARDING FEDERALLY SPONSORED RESEARCH OR DEVELOPMENT

This invention was supported by the National Institute of Health, Grant No. R21-CA-109907, and the National Science Foundation, Grant No. BES-03-48204. The United States Government has certain rights in the invention.

FIELD

Fourier domain angle-resolved low coherence interferometry (faLCI) system and method that enables data acquisition of angle-resolved and depth-resolved spectra information of a sample, in which depth and size information about the sample can be obtained with a single scan at rapid rates for in vivo applications in particular.

BACKGROUND

Examining the structural features of cells is essential for many clinical and laboratory studies. The most common tool used in the examination for the study of cells has been the microscope. Although microscope examination has led to great advances in understanding cells and their structure, it is inherently limited by the artifacts of preparation. The characteristics of the cells can only been seen at one moment in time with their structure features altered because of the addition of chemicals. Further, invasion is necessary to obtain the cell sample for examination.

Thus, light scattering spectrography (LSS) was developed to allow for in vivo examination applications, including cells. The LSS technique examines variations in the elastic scattering properties of cell organelles to infer their sizes and other dimensional information. In order to measure cellular features in tissues and other cellular structures, it is necessary to distinguish the singly scattered light from diffuse light, which has been multiply scattered and no longer carries easily accessible information about the scattering objects. This distinction or differentiation can be accomplished in several ways, such as the application of a polarization grating, by restricting or limiting studies and analysis to weakly scattering samples, or by using modeling to remove the diffuse component(s).

As an alternative approach for selectively detecting singly scattered light from sub-surface sites, low-coherence interferometry (LCI) has also been explored as a method of LSS. LCI utilizes a light source with low temporal coherence, such as broadband white light source for example. Interference is only achieved when the path length delays of the interferometer are matched with the coherence time of the light source. The axial resolution of the system is determined by the coherent length of the light source and is typically in the micrometer range suitable for the examination of tissue samples. Experimental results have shown that using a broadband light source and its second harmonic allows the recovery of information about elastic scattering using LCI. LCI has used time depth scans by moving the sample with respect to a reference arm directing the light source onto the sample to receive scattering information from a particular point on the sample. Thus, scan times were on the order of 5-30 minutes in order to completely scan the sample.

Angle-resolved LCI (a/LCI) has been developed as a means to obtain sub-surface structural information regarding the size of a cell. Light is split into a reference and sample beam, wherein the sample beam is projected onto the sample at different angles to examine the angular distribution of scattered light. The a/LCI technique combines the ability of (LCI) to detect singly scattered light from sub-surface sites with the capability of light scattering methods to obtain structural information with sub-wavelength precision and accuracy to construct depth-resolved tomographic images. Structural information is determined by examining the angular distribution of the back-scattered light using a single broadband light source is mixed with a reference field with an angle of propagation. The size distribution of the cell is determined by comparing the osciallary part of the measured angular distributions to predictions of Mie theory. Such a system is described in *Cellular Organization and Substructure Measured Using Angle-Resolved Low-Coherence Inteferometry*, Biophysical Journal, 82, April 2002, 2256-2265, incorporated herein by reference in its entirety.

The a/LCI technique has been successfully applied to measuring cellular morphology and to diagnosing intraepithelial neoplasia in an animal model of carcinogenesis. The inventors of the present application described such a system in *Determining nuclear morphology using an improved angle-resolved low coherence interferometry system* in Optics Express, 2003, 11(25): p. 3473-3484, incorporated herein by reference in its entirety. The a/LCI method of obtaining structural information about a sample has been successfully applied to measuring cellular morphology in tissues and in vitro as well as diagnosing intraepithelial neoplasia and assessing the efficacy of chemopreventive agents in an animal model of carcinogenesis. a/LCI has been used to prospectively grade tissue samples without tissue processing, demonstrating the potential of the technique as a biomedical diagnostic.

Initial prototype and second generation a/LCI systems required 30 and 5 minutes respectively to obtain similar data. These earlier systems relied on time domain depth scans just as provided in previous LCI based systems. The length of the reference arm of the interferometer had to be mechanically adjusted to achieve serial scanning of the detected scattering angle. The method of obtaining angular specificity was achieved by causing the reference beam of the interferometry scheme to cross the detector plane at a variable angle. This general method for obtaining angle-resolved, depth-resolved backscattering distributions was disclosed in U.S. Pat. No. 6,847,456 entitled "Methods and systems using field-based light scattering spectroscopy," which is incorporated by reference herein in its entirety.

Other LCI prior systems are disclosed in U.S. Pat. Nos. 6,002,480 and 6,501,551, both of which are incorporated by reference herein in their entireties. U.S. Pat. No. 6,002,480 covers obtaining depth-resolved spectroscopic distributions and discusses obtaining the size of scatterers by observing changes in wavelength due to elastic scattering properties. U.S. Pat. No. 6,501,551 covers endoscopic application of interferometric imaging and does anticipate the use of Fourier domain concepts to obtain depth resolution. U.S. Pat. No. 6,501,551 does not discuss measurement of angularly resolved scattering distributions, the use of scattered light to determine scatterer size by analysis of elastic scattering properties, nor the use of an imaging spectrometer to record data in parallel, whether that data is scattering or imaging data. Finally, U.S. Pat. No. 7,061,622 discusses fiber optic means for measuring angular scattering distributions, but does not discuss the Fourier domain concept. Also because it describes an imaging technique, the embodiments all include focusing optics which limit the region probed.

SUMMARY OF THE DETAILED DESCRIPTION

Embodiments disclosed herein involve a new a/LCI technique called Fourier domain a/LCI (faLCI), which enables data acquisition at rapid rates using a single scan, sufficient to make in vivo applications feasible. The embodiments disclosed herein obtain angle-resolved and depth-resolved spectra information about a sample, in which depth and size information about the sample can be obtained with a single scan, and wherein the reference arm can remain fixed with respect to the sample due to only one scan required. A reference signal and a reflected sample signal are cross-correlated and dispersed at a multitude of reflected angles off of the sample, thereby representing reflections from a multitude of points on the sample at the same time in parallel.

Since this angle-resolved, cross-correlated signal is spectrally dispersed, the new data acquisition scheme is significant as it permits data to be obtained in less than one second, a threshold determined to be necessary for acquiring data from in vivo tissues. Information about all depths of the sample at each of the multitude of different points on the sample can be obtained with one scan on the order of approximately 40 milliseconds. From the spatial, cross-correlated reference signal, structural (size) information can also be obtained using techniques that allow size information of scatterers to be obtained from angle-resolved data.

The faLCI technique of the disclosed embodiments uses the Fourier domain concept to acquire depth resolved information. Signal-to-noise and commensurate reductions in data acquisition time are possible by recording the depth scan in the Fourier (or spectral) domain. The faLCI system combines the Fourier domain concept with the use of an imaging spectrograph to spectrally record the angular distribution in parallel. Thereafter, the depth-resolution of the disclosed embodiments is achieved by Fourier transforming the spectrum of two mixed fields with the angle-resolved measurements obtained by locating the entrance slit of the imaging spectrograph in a Fourier transform plane to the sample. This converts the spectral information into depth-resolved information and the angular information into a transverse spatial distribution. The capabilities of faLCI have been initially demonstrated by extracting the size of polystyrene beads in a depth-resolved measurement.

Various mathematical techniques and methods are provided for determining size information of the sample using the angle-resolved, cross-correlated signal.

The embodiments disclosed herein are not limited to any particular arrangement. In one embodiment, the apparatus is based on a modified Mach-Zehnder interferometer, wherein broadband light from a superluminescent diode is split into a reference beam and an input beam to the sample by a beamsplitter. In another embodiment, a unique optical fiber probe can be used to deliver light and collect the angular distribution of scattered light from the sample of interest.

The a/LCI method can be a clinically viable method for assessing tissue health without the need for tissue extraction via biopsy or subsequent histopathological evaluation. The a/LCI system can be applied for a number of purposes: early detection and screening for dysplastic epithelial tissues, disease staging, monitoring of therapeutic action and guiding the clinician to biopsy sites. The non-invasive, non-ionizing nature of the optical a/LCI probe means that it can be applied frequently without adverse affect. The potential of a/LCI to provide rapid results will greatly enhance its widespread applicability for disease screening.

BRIEF DESCRIPTION OF THE FIGURES

The accompanying drawing figures incorporated in and forming a part of this specification illustrate several aspects of the disclosed embodiments, and together with the description serve to explain the principles of the disclosed embodiments.

FIG. 8A is an illustration of an alternative fiber-optic faLCI system that may be employed with the disclosed embodiments;

FIG. 8B is an illustration of sample illumination and scattered light collection with distal end of probe in the faLCI system illustrated in FIG. 8B; and FIG. 8C is an illustration of an image of the illuminated distal end of probe of the faLCI system illustrated in FIG. 8A.

DETAILED DESCRIPTION

Figure 1A:
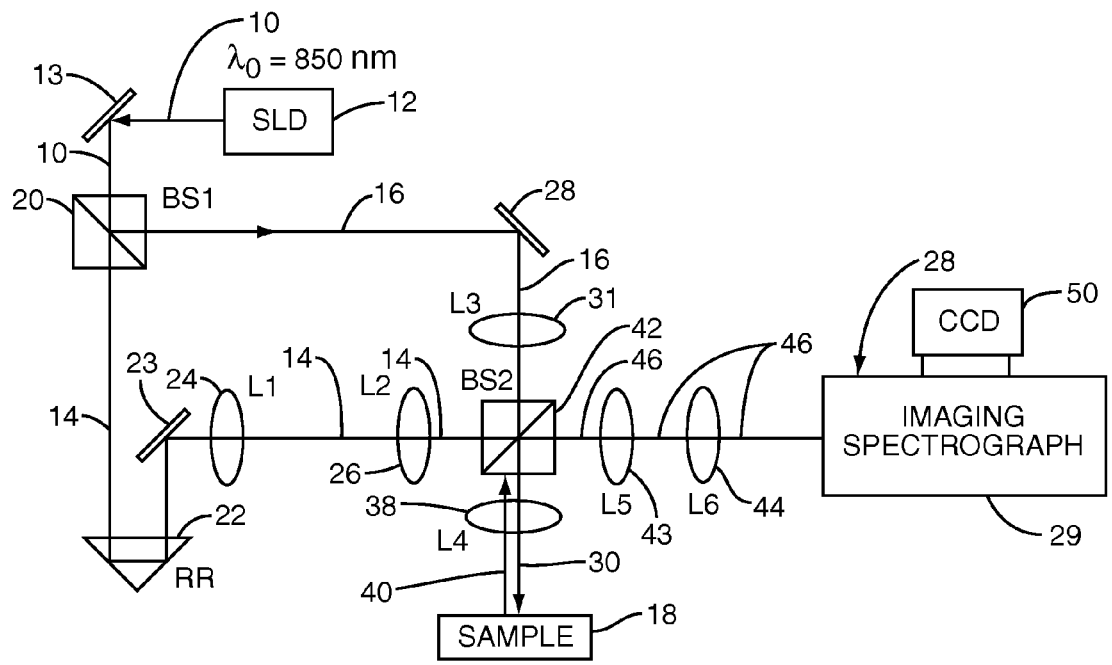
FIG. 1A is a schematic of one exemplary embodiment of the faLCI system employing Mach-Zehnder interferometer.

The embodiments set forth below represent the necessary information to enable those skilled in the art to practice the disclosed embodiments and illustrate the best mode of practicing the embodiments. Upon reading the following description in light of the accompanying drawing figures, those skilled in the art will understand the concepts of the embodiments and will recognize applications of these concepts not particularly addressed herein. It should be understood that these concepts and applications fall within the scope of the disclosure and the accompanying claims.

Embodiments disclosed herein involve a new a/LCI technique called Fourier domain a/LCI (faLCI), which enables data acquisition at rapid rates using a single scan, sufficient to make in vivo applications feasible. The embodiments disclosed herein obtain angle-resolved and depth-resolved spectra information about a sample, in which depth and size information about the sample can be obtained with a single scan, and wherein the reference arm can remain fixed with respect to the sample due to only one scan required. A reference signal and a reflected sample signal are cross-correlated and dispersed at a multitude of reflected angles off of the sample, thereby representing reflections from a multitude of points on the sample at the same time in parallel.

Since this angle-resolved, cross-correlated signal is spectrally dispersed, the new data acquisition scheme is significant as it permits data to be obtained in less than one second, a threshold determined to be necessary for acquiring data from in vivo tissues. Information about all depths of the sample at each of the multitude of different points on the sample can be obtained with one scan on the order of approximately 40 milliseconds. From the spatial, cross-correlated reference signal, structural (size) information can also be obtained using techniques that allow size information of scatterers to be obtained from angle-resolved data.

The faLCI technique of the disclosed embodiments uses the Fourier domain concept to acquire depth resolved information. Signal-to-noise and commensurate reductions in data acquisition time are possible by recording the depth scan in the Fourier (or spectral) domain. The faLCI system combines the Fourier domain concept with the use of an imaging spectrograph to spectrally record the angular distribution in parallel. Thereafter, the depth-resolution of the disclosed embodiments is achieved by Fourier transforming the spectrum of two mixed fields with the angle-resolved measurements obtained by locating the entrance slit of the imaging spectrograph in a Fourier transform plane to the sample. This converts the spectral information into depth-resolved information and the angular information into a transverse spatial distribution. The capabilities of faLCI have been initially demonstrated by extracting the size of polystyrene beads in a depth-resolved measurement.

The key advances of the disclosed embodiments can be broken down into three components: (1) new rapid data acquisition methods, (2) fiber probe designs, and (3) data analysis schemes. Thus, the disclosed embodiments are described in this matter for convenience in its understanding.

Figure 2:
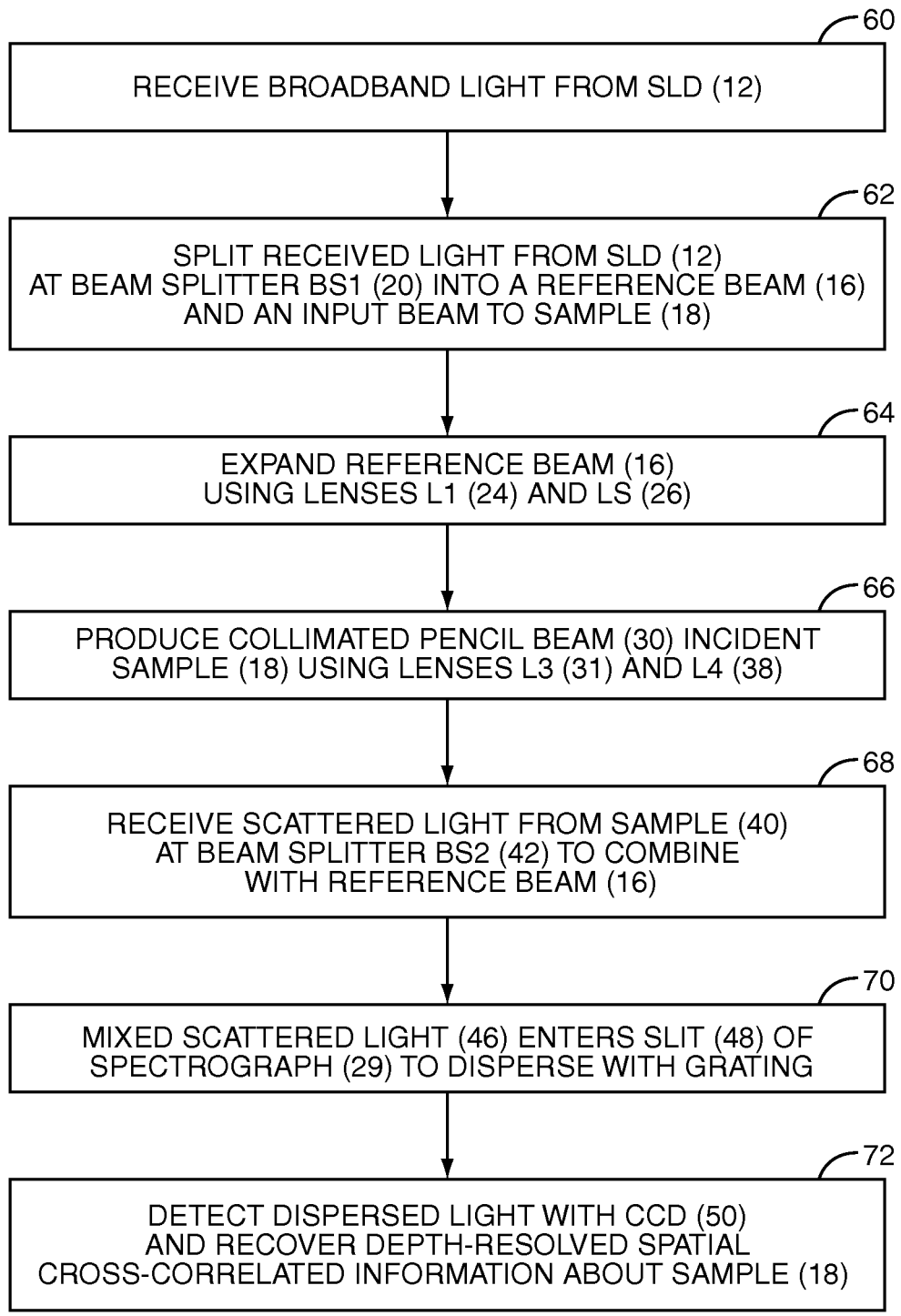
FIG. 2 is a flowchart illustrating the steps performed by the interferometer apparatus to recover depth-resolved spatial cross-correlated information about the sample for analysis.

An exemplary apparatus, as well as the steps involved in the process of obtaining angle and depth-resolved distribution data scattered from a sample, are also set forth in FIG. 2. The faLCI scheme in accordance with one embodiment of the disclosed embodiments is based on a modified Mach-Zehnder interferometer as illustrated in FIG. 1A. Broadband light 10 from a superluminescent diode (SLD) 12 is directed by a mirror 13 (step 60 in FIG. 2) and split into a reference beam 14 and an input beam 16 to a sample 18 by beamsplitter BS1 20 (step 62 in FIG. 3). The output power of the SLD 12 may be 3 milliWatts, having a specification of $\lambda_o$=850 nm, $\Delta\lambda$=20 nm FWHM for example, providing sufficiently low coherence length to isolate scattering from a cell layer within tissue. The path length of the reference beam 14 is set by adjusting retroreflector RR 22, but remains fixed during measurement. The reference beam 14 is expanded using lenses L1 (24) and L2 (26) to create illumination (step 64 in FIG. 2), which is uniform and collimated upon reaching a spectrograph slit 48 in an imaging spectrograph 29. For example, L1 may have a focal length of 1.5 centimeters, and L2 26 may have focal length of 15 centimeters.

Lenses L3 (31) and L4 (38) are arranged to produce a collimated pencil beam 30 incident on the sample 18 (step 66 in FIG. 2). By displacing lens L4 (38) vertically relative to lens L3 (31), the input beam 30 is made to strike the sample at an angle of 0.10 radians relative to the optical axis. This arrangement allows the full angular aperture of lens L4 (38) to be used to collect scattered light 40 from the sample 18. Lens L4 (38) may have a focal length of 3.5 centimeters.

Figure 1B:
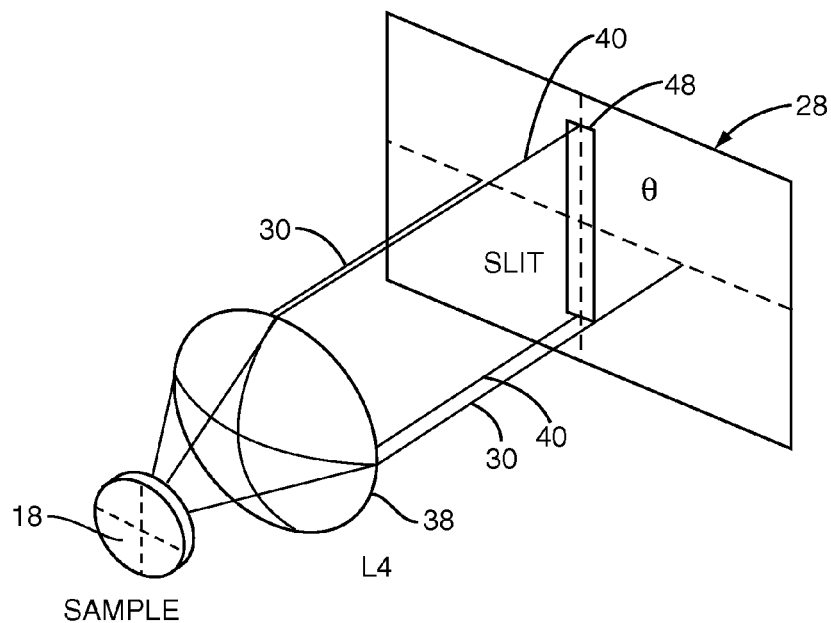
FIG. 1B is an illustration showing the relationship of the detected scattering angle to slit of spectrograph in the interferometer arrangement of FIG. 1A.

The light 40 scattered by the sample 18 is collected by lens L4 (32) and relayed by a 4f imaging system comprised of lenses L5 (43) and L6 (44) such that the Fourier plane of lens L4 (32) is reproduced in phase and amplitude at the spectrograph slit 48 (step 68 in FIG. 2). The scattered light 40 is mixed with the reference field 14 at a second beamsplitter BS2 42 with the combined fields 46 falling upon the entrance slit (illustrated in FIG. 1B as element 48) to the imaging spectrograph 29 (step 70 in FIG. 2). The imaging spectrograph 29 may be the model SP2150i, manufactured by Acton Research for example. FIG. 1B illustrates the distribution of scattering angle across the dimension of the slit 48. The mixed fields are dispersed with a high resolution grating (e.g. 1200 l/mm) and detected using a cooled CCD 50 (e.g. 1340×400, 20 μm×20 μm pixels, Spec10:400, manufactured by Princeton Instruments) (step 72 in FIG. 2).

The detected signal 46 is a function of vertical position on the spectrograph slit 48, y, and wavelength $\lambda$ once the light is dispersed by the spectrograph 29. The detected signal at pixel (m, n) can be related to the signal 40 and reference fields 16 ($E_s$, $E_r$) as:

$$I(\lambda_m, y_n) = \langle |E_r(\lambda_m, y_n)|^2 \rangle + \langle |E_s(\lambda_m, y_n)|^2 \rangle + 2Re\langle E_s(\lambda_m, y_n) E_r^*(\lambda_m, y_n)\rangle \cos\phi, \quad (1)$$

where $\phi$ is the phase difference between the two fields 30, 16 and $\langle \ldots \rangle$ denotes an ensemble average in time. The interference term is extracted by measuring the intensity of the signal 30 and reference beams 16 independently and subtracting them from the total intensity.

In order to obtain depth resolved information, the wavelength spectrum at each scattering angle is interpolated into a wavenumber ($k=2\pi/\lambda$) spectrum and Fourier transformed to give a spatial cross correlation, $\Gamma_{SR}(z)$ for each vertical pixel $y_n$:

$$\Gamma_{SR}(z, y_n) = \int dk e^{ikz} \langle E_s(k, y_n) E_r^*(k, y_n)\rangle \cos\phi. \quad (2)$$

The reference field 14 takes the form:

$$E_r(k) = E_o \exp[-((k-k_o)/\Delta k)^2] \exp[-((y-y_o)/\Delta y)^2] \exp[ik\Delta l] \quad (3)$$

where $k_o$ ($y_o$) and $\Delta k$ ($\Delta y$) represent the center and width of the Gaussian wavevector (spatial) distribution and $\Delta l$ is the selected path length difference. The scattered field 40 takes the form $$E_s(k,\theta) = \Sigma_j E_o \exp[-((k-k_o)/\Delta k)^2] \exp[ikl_j] S_j(k,\theta) \quad (4)$$

where $S_j$ represents the amplitude distribution of the scattering originating from the jth interface, located at depth $l_j$. The angular distribution of the scattered field 40 is converted into a position distribution in the Fourier image plane of lens L4 through the relationship $y=f_4\theta$. For the pixel size of the CCD 50 (e.g. 20 μm), this yields an angular resolution (e.g. 0.57 mrad) and an expected angular range (e.g. 228 mrad.).

Inserting Eqs. (3) and (4) into Eq. (2) and noting the uniformity of the reference field 14 ($\Delta y$>>>slit height) yields the spatial cross correlation at the nth vertical position on the detector 29:

$$\Gamma_{SR}(z, y_n) = \sum_j \int dk |E_o|^2 \exp[-2((k-k_o)/\Delta k)^2] \quad (5)$$

$$\exp[ik(z - \Delta l + l_j)] \times S_j(k, \theta_n = y_n/f_4)\cos\phi.$$

Evaluating this equation for a single interface yields:

$$\Gamma_{SR}(z,y_n) = |E_o|^2 \exp[-((z-\Delta l + l_j)\Delta k)^2/8] S_j(k_o,\theta_n=y_n/f_4) \cos\phi. \quad (6)$$

Here we have assumed that the scattering amplitude S does not vary appreciably over the bandwidth of the source light 12. This expression shows that we obtain a depth resolved profile of the scattering distribution 40 with each vertical pixel corresponding to a scattering angle.

Figure 3A:
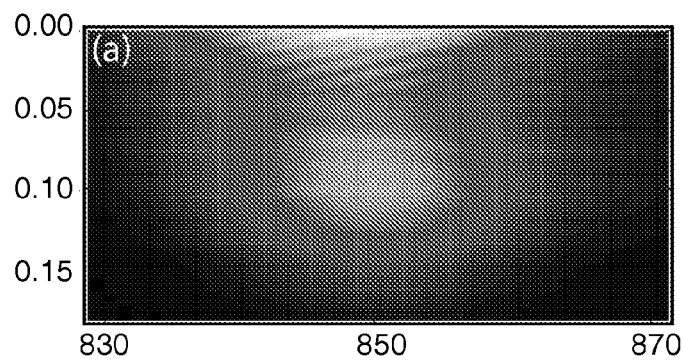
FIGS. 3A-D illustrate examples of faLCI data recovered in the spectral domain for an exemplary sample of polystyrene beads, comprising the total acquired signal (FIG. 3A), the reference field intensity (FIG. 3B), the signal field intensity (FIG. 3C), and the extracted, cross-correlated signal between the reference and signal field intensities (FIG. 3D)

FIG. 3A below shows typical data representing the total detected intensity (Equation (1), above) of the sum of the reference field 16 and the field scattered 40 by a sample of polystyrene beads, in the frequency domain given as a function of wavelength and angle, given with respect to the backwards scattering direction. In an exemplary embodiment, this data was acquired in 40 milliseconds and records data over 186 mrad, approximately 85% of the expected range, with some loss of signal at higher angles.

Figure 3B:
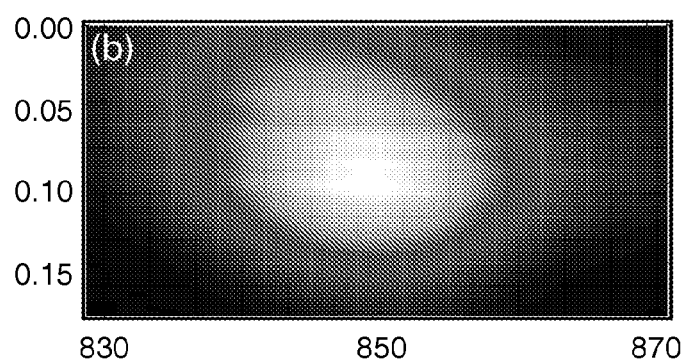
Figure 3C:
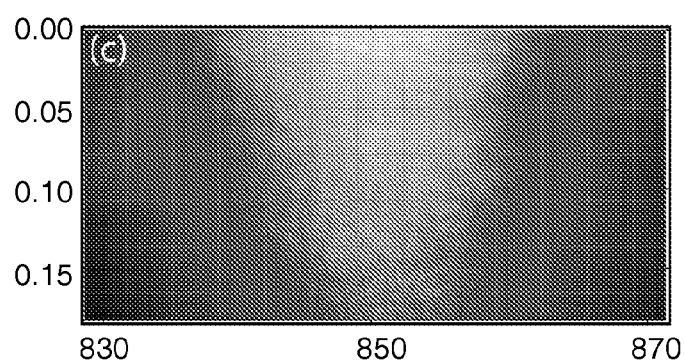
Figure 3D:
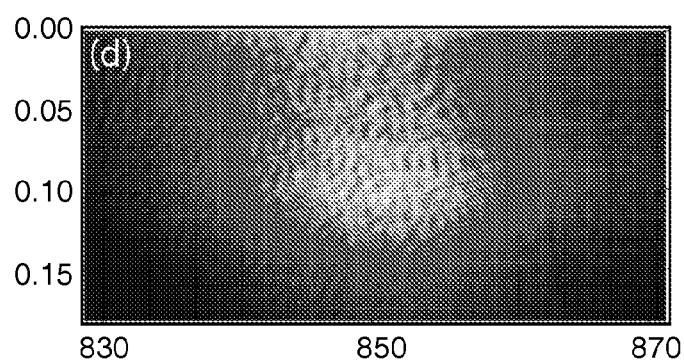
Figure 4A:
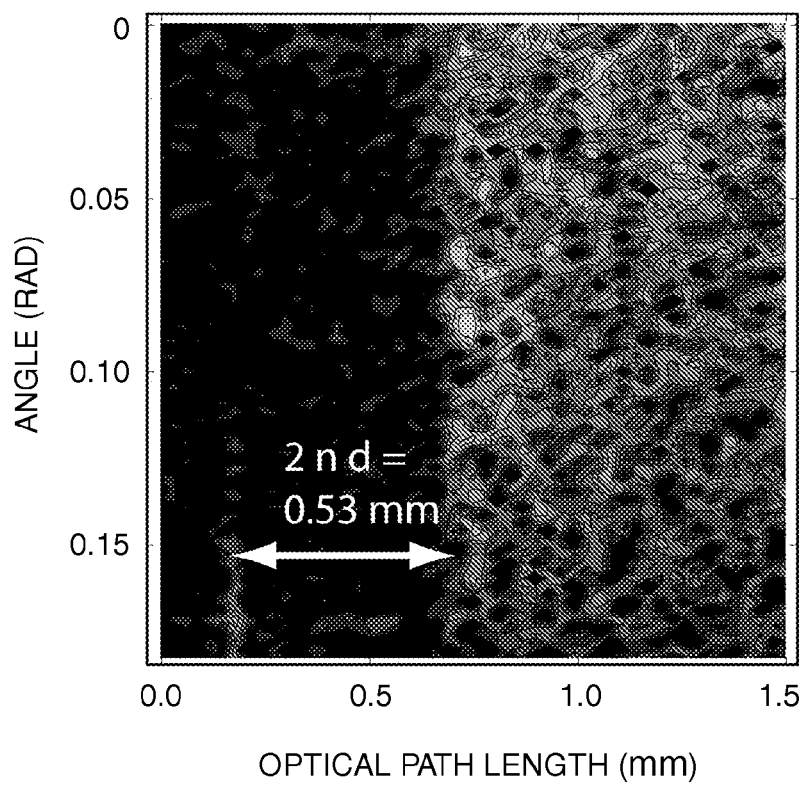
FIG. 4A is an illustration of the axial spatial cross-correlated function performed on the cross-correlated faLCI data illustrated in FIG. 3D as a function of depth and angle.

FIGS. 3B and 3C illustrate the intensity of the reference and signal fields 14, respectively. Upon subtraction of the signal and reference fields 14, 30 from the total detected intensity, the interference 46 between the two fields is realized as illustrated in FIG. 3D. At each angle, interference data 46 are interpolated into k-space and Fourier transformed to give the angular depth resolved profiles of the sample 18 as illustrated in FIG. 4A. The Fourier transform of the angle-resolved, cross correlated signal 46, which is the result of signal 40 scattered at a multitude of reflected angles off the sample 18 and obtained in the Fourier plane of lens L4 (38), produces depth-resolved information about the sample 18 as a function of angle and depth. This provides depth-resolved information about the sample 18. Because the angle-resolved, cross-correlated signal 46 is spectrally dispersed, the data acquisition permits data to be obtained in less than one second. Information about all depths of the sample 18 at each of the multitude of different points (i.e. angles) on the sample 18 can be obtained with one scan on the order of approximately 40 milliseconds. Normally, time domain based scanning is required to obtain information about all depths of a sample at a multitude of different points, thus requiring substantial time and movement of the reference arm with respect to the sample.

In the experiments that produced the depth-resolved profile of the sample 18 illustrated in FIG. 4A, the sample 18 consists of polystyrene microspheres (e.g. n=1.59, 10.1 μm mean diameter, 8.9% variance, NIST certified, Duke Scientific) suspended in a mixture of 80% water and 20% glycerol (n=1.36) to provide neutral buoyancy. The solution was prepared to obtain a scattering length l=200 μm. The sample is contained in a round well (8 mm diameter, 1 mm deep) behind a glass coverslip (thickness, d~170 μm) (not shown). The sample beam 30 is incident on the sample 18 through the coverslip. The round trip thickness through the coverslip (2 n d=2 (1.5) (170 μm)=0.53 mm—see FIG. 4A) shows the depth resolved capability of the approach. The data are ensemble averaged by integrating over one mean free path (MFP). The spatial average can enable a reduction of speckle when using low-coherence light to probe a scattering sample. To simplify the fitting procedure, the scattering distribution is low pass filtered to produce a smoother curve, with the cutoff frequency chosen to suppress spatial correlations on length scales above 16 μm.

Figure 4B:
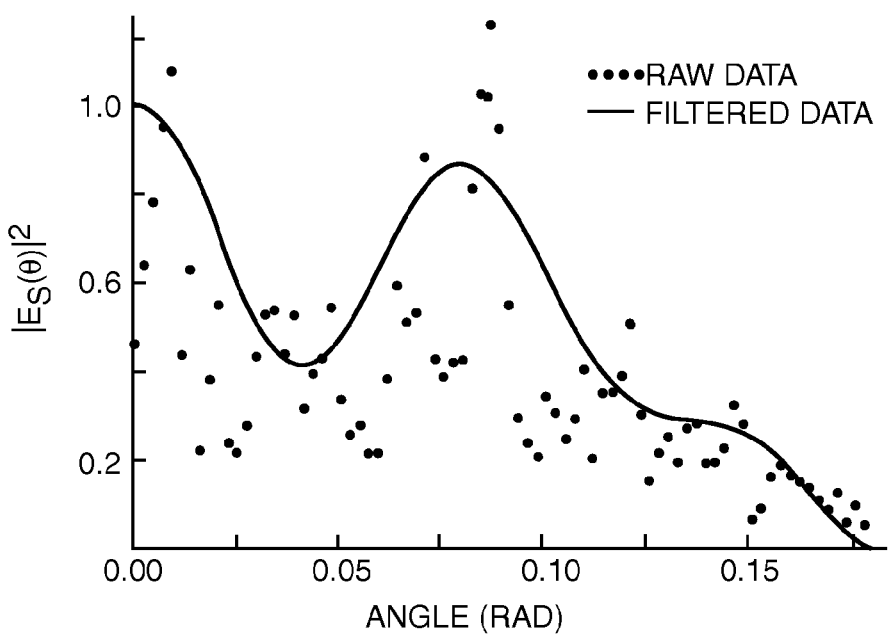
FIG. 4B is an illustration of an angular distribution plot of raw and filtered data regarding scattered sample signal intensity as a function of angle in order to recover size information about the sample.

In addition to obtaining depth-resolved information about the sample 18, the scattering distribution data (i.e. a/LCI data) obtained from the sample 18 using the disclosed data acquisition scheme can also be used to make a size determination of the nucleus using the Mie theory. A scattering distribution 74 of the sample 18 is illustrated in FIG. 4B as a contour plot. The raw scattered information 74 about the sample 18 is shown as a function of the signal field 30 and angle. A filtered curve is determined using the scattered data 74. Comparison of the filtered scattering distribution curve 76 (i.e. a representation of the scattered data 74) to the prediction of Mie theory (curve 78 in FIG. 5A) enables a size determination to be made.

In order to fit the scattered data 76 to Mie theory, the a/LCI signals are processed to extract the oscillatory component which is characteristic of the nucleus size. The smoothed data 76 are fit to a low-order polynomial ($4^{th}$ order was used for example herein, but later studies use a lower $2^{nd}$ order), which is then subtracted from the distribution 76 to remove the background trend. The resulting oscillatory component is then compared to a database of theoretical predictions obtained using Mie theory 78 from which the slowly varying features were similarly removed for analysis.

A direct comparison between the filtered a/LCI data 76 and Mie theory data 78 may not possible, as the chi-squared fitting algorithm tends to match the background slope rather than the characteristic oscillations. The calculated theoretical predictions include a Gaussian distribution of sizes characterized by a mean diameter (d) and standard deviation (ED) as well as a distribution of wavelengths, to accurately model the broad bandwidth source.

The best fit (FIG. 5A) is determined by minimizing the Chi-squared between the data 76 and Mie theory (FIG. 5B), yielding a size of 10.2+/−1.7 μm, in excellent agreement with the true size. The measurement error is larger than the variance of the bead size, most likely due to the limited range of angles recorded in the measurement.

As an alternative to processing the a/LCI data and comparing to Mie theory, there are several other approaches which could yield diagnostic information. These include analyzing the angular data using a Fourier transform to identify periodic oscillations characteristic of cell nuclei. The periodic oscillations can be correlated with nuclear size and thus will possess diagnostic value. Another approach to analyzing a/LCI data is to compare the data to a database of angular scattering distributions generated with finite element method (FEM) or T-Matrix calculations. Such calculations may offer superior analysis as there are not subject to the same limitations as Mie theory. For example, FEM or T-Matrix calculations can model non-spherical scatterers and scatterers with inclusions while Mie theory can only model homogenous spheres.

As an alternative embodiment, the disclosed embodiments can also employ optical fibers to deliver and collect light from the sample of interest to use in the a/LCI system for endoscopic applications. This alternative embodiment is illustrated in FIG. 6.

The fiber optic a/LCI scheme for this alternative embodiment makes use of the Fourier transform properties of a lens. This property states that when an object is placed in the front focal plane of a lens, the image at the conjugate image plane is the Fourier transform of that object. The Fourier transform of a spatial distribution (object or image) is given by the distribution of spatial frequencies, which is the representation of the image's information content in terms of cycles per mm. In an optical image of elastically scattered light, the wavelength retains its fixed, original value and the spatial frequency representation is simply a scaled version of the angular distribution of scattered light.

In the fiber optic a/LCI scheme, the angular distribution is captured by locating the distal end of the fiber bundle in a conjugate Fourier transform plane of the sample using a collecting lens. This angular distribution is then conveyed to the distal end of the fiber bundle where it is imaged using a 4f system onto the entrance slit of an imaging spectrograph. A beamsplitter is used to overlap the scattered field with a reference field prior to entering the slit so that low coherence interferometry can also be used to obtain depth resolved measurements.

Figure 6:
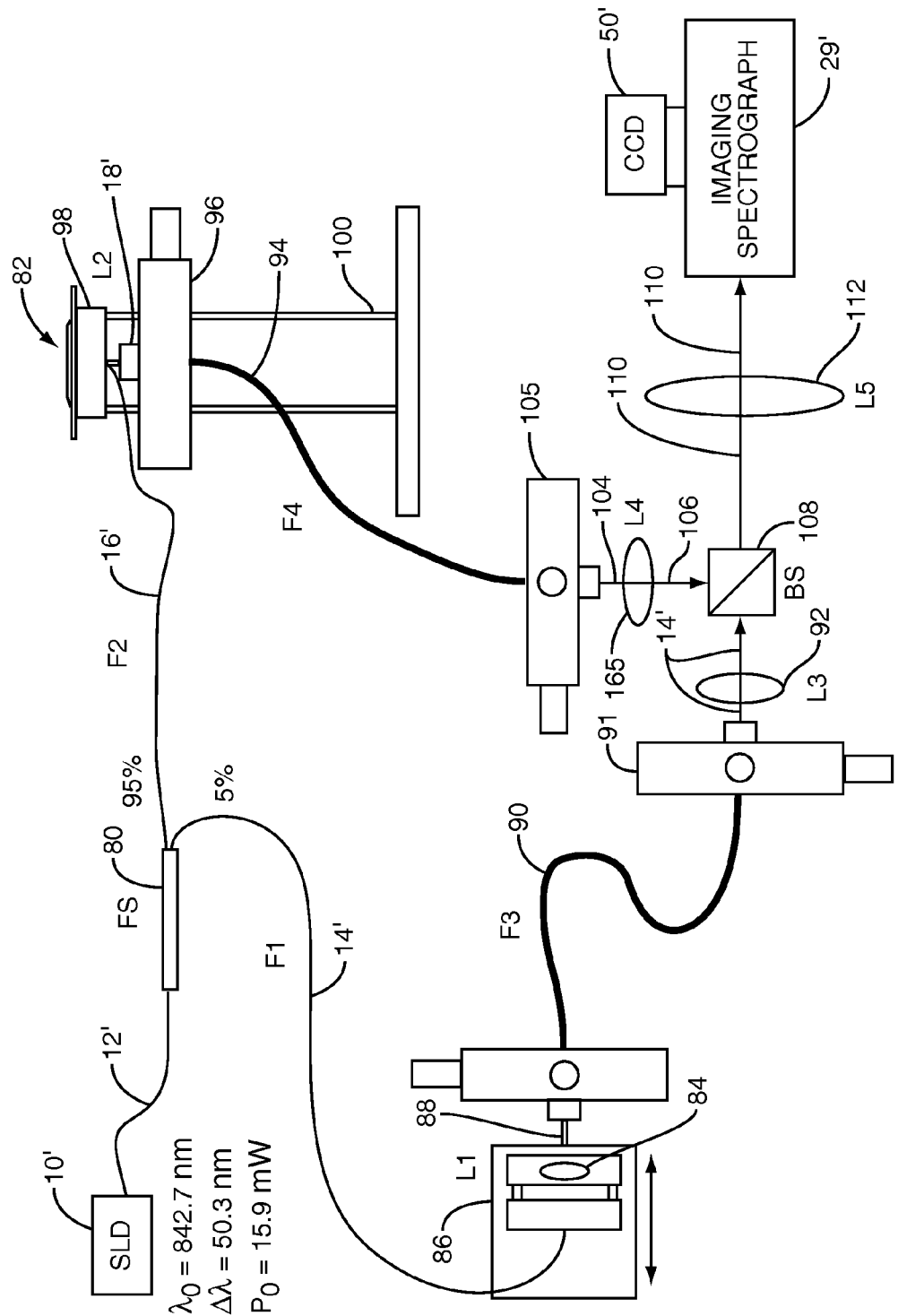
FIG. 6 is a schematic of exemplary embodiment of the faLCI system employing an optical fiber probe.

Turning now to FIG. 6, the fiber optic faLCI scheme is shown. Light 12' from a broadband light source 10' is split into a reference field 14' and a signal field 16' using a fiber splitter (FS) 80. A splitter ratio of 20:1 is chosen in one embodiment to direct more power to a sample 18' via the signal arm 82 as the light returned by the tissue is typically only a small fraction of the incident power.

Light in the reference fiber 14' emerges from fiber F1 and is collimated by lens L1 (84) which is mounted on a translation stage 86 to allow gross alignment of the reference arm path length. This path length is not scanned during operation but may be varied during alignment. A collimated beam 88 is arranged to be equal in dimension to the end 91 of fiber bundle F3 (90) so that the collimated beam 88 illuminates all fibers in F3 with equal intensity. The reference field 14' emerging from the distal tip of F3 (90) is collimated with lens L3 (92) in order to overlap with the scattered field conveyed by fiber F4 (94). In an alternative embodiment, light emerging from fiber F1 (14') is collimated then expanded using a lens system to produce a broad beam.

Figure 7A:
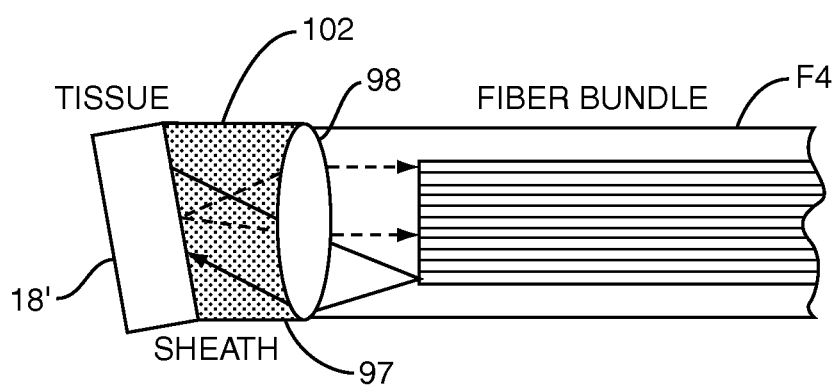
FIG. 7A is a cutaway view of an a/LCI fiber-optic probe tip that may be employed by the faLCI system illustrated in FIG. 6.

The scattered field is detected using a coherent fiber bundle. The scattered field is generated using light in the signal arm 82 which is directed toward the sample 18' of interest using lens L2 (98). As with the free space system, lens L2 (98) is displaced laterally from the center of single-mode fiber F2 such that a collimated beam is produced which is traveling at an angle relative to the optical axis The fact that the incident beam strikes the sample at an oblique angle is essential in separating the elastic scattering information from specular reflections. The light scattered by the sample 18' is collected by a fiber bundle consisting of an array of coherent single mode or multi-mode fibers. The distal tip of the fiber is maintained one focal length away from lens L2 (98) to image the angular distribution of scattered light. In the embodiment shown in FIG. 6, the sample 18' is located in the front focal plane of lens L2 (98) using a mechanical mount 100. In the endoscope compatible probe shown in FIG. 7, the sample is located in the front focal plane of lens L2 (98) using a transparent sheath (element 102).

Figure 7B:
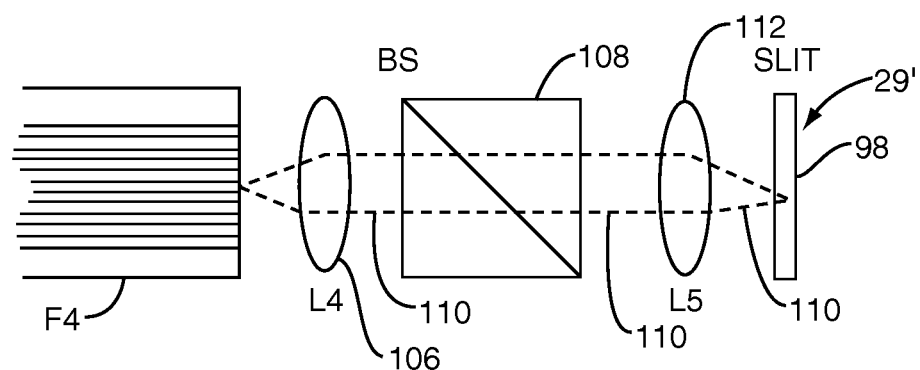
FIG. 7B illustrates the location of the fiber probe in the faLCI system illustrated in FIG. 7A.

As illustrated in FIG. 6 and also FIG. 7B, scattered light 104 emerging from a proximal end 105 of the fiber probe F4 (94) is recollimated by lens L4 (104) and overlapped with the reference field 14' using beamsplitter BS (108). The two combined fields 110 are re-imaged onto the slit (element 48' in FIG. 7) of the imaging spectrograph 29' using lens L5 (112). The focal length of lens L5 (112) may be varied to optimally fill the slit 48'. The resulting optical signal contains information on each scattering angle across the vertical dimension of the slit 48' as described above for the apparatus of FIGS. 1A and 1B.

It is expected that the above-described a/LCI fiber-optic probe will collect the angular distribution over a 0.45 radian range (approx. 30 degrees) and will acquire the complete depth resolved scattering distribution 110 in a fraction of a second.

There are several possible schemes for creating the fiber probe which are the same from an optical engineering point of view. One possible implementation would be a linear array of single mode fibers in both the signal and reference arms. Alternatively, the reference arm 96 could be composed of an individual single mode fiber with the signal arm 82 consisting of either a coherent fiber bundle or linear fiber array.

The fiber probe tip can also have several implementations which are substantially equivalent. These would include the use of a drum or ball lens in place of lens L2 (98). A side-viewing probe could be created using a combination of a lens and a minor or prism or through the use of a convex minor to replace the lens-minor combination. Finally, the entire probe can be made to rotate radially in order to provide a circumferential scan of the probed area.

Figure 5A:
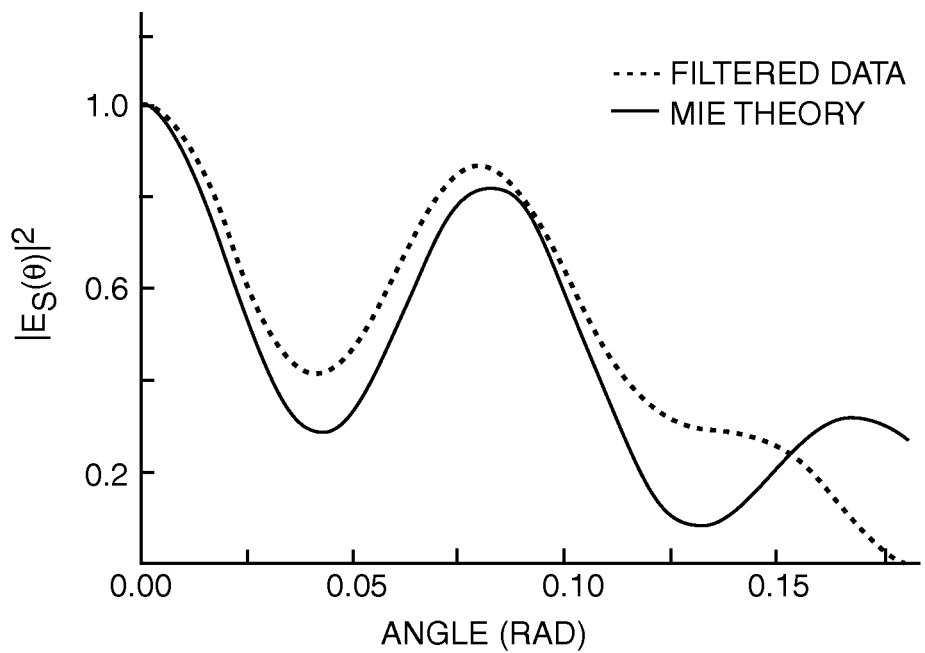
FIG. 5A is an illustration of the filtered angular distribution of the scattered sample signal intensity compared to the best fit Mie theory to determine size information about the sample.
Figure 5B:
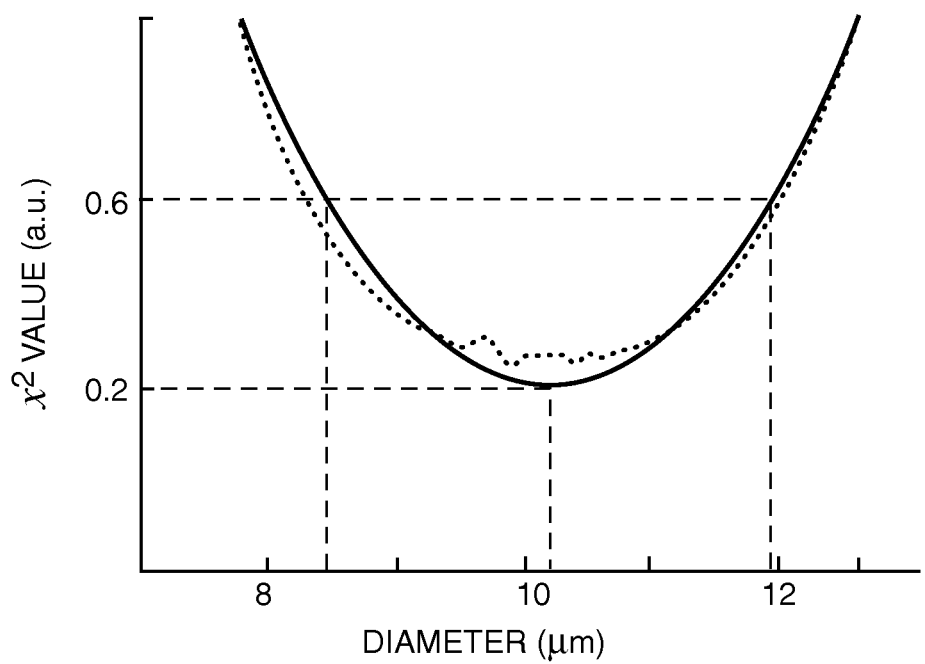
FIG. 5B is a Chi-squired minimization of size information about the sample to estimate the diameter of cells in the sample.

Yet another data acquisition embodiment of the disclosed embodiments could be a fa/LCI system is based on a modified Mach-Zehnder interferometer as illustrated in FIG. 5A. The output 10" from a fiber-coupled superluminescent diode (SLD) source 12" (e.g. Superlum, $P_o$=15 mW, $\lambda o$=841.5 nm, $\Delta\lambda$=49.5 nm, coherence length=6.3 µm) is split into sample arm delivery fiber 16" and a reference arm delivery fiber 14" by a 90/10 fiber splitter FS (80') (e.g. manufactured by AC Photonics). The sample arm delivery fiber 16" can consist of either of the following for example: (1) a single mode fiber with polarization control integrated at the tip; or (2) a polarization maintaining fiber. A sample probe 113 is assembled by affixing the delivery fiber 16"(NA≅0.12) along the ferrule 114 at the distal end of a fiber bundle 116 such that the end face of the delivery fiber 16" is parallel to and flush with the face of the fiber bundle 116. Ball lens L1 (115) (e.g. f=2.2 mm) is positioned one focal length from the face of the probe 113 and centered on the fiber bundle 116, offsetting the delivery fiber 16" from the optical axis of lens L1 (115). This configuration, which is also depicted in FIG. 8B, produces a collimated beam 120 (e.g. P=9 mW) with a diameter (e.g. $2f_1 NA$) of 0.5 mm incident on the sample 18" at an angle of 0.25 rad. for example.

The scattered light 122 from the sample is collected by lens L1 (115) and, via the Fourier transform property of the lens L1 (115, the angular distribution of the scattered field 122 is converted into a spatial distribution at the distal face of the multimode coherent fiber bundle 116 (e.g. Schott North America, Inc., length=840 mm, pixel size=8.2 µm, pixel count=13.5K) which is located at the Fourier image plane of lens L1 (115). The relationship between vertical position on the fiber bundle, y', and scattering angle, θ is given by y'=f₁θ. As an illustration, the optical path of light scattered 122 at three selected scattering angles is shown in FIG. 8B. Overall, the angular distribution is sampled by approximately 130 individual fibers for example, across a vertical strip of the fiber bundle 116", as depicted by the highlighted area in FIG. 8C. The 0.2 mm, for example, thick ferrule ($d_1$) separating the delivery fiber 16" and fiber bundle 116 limits the minimum theoretical collection angle ($\theta_{min,th}=d_1/f_1$) to 0.09 rad in this example. The maximum theoretical collection angle is determined by $d_1$ and $d_2$, the diameter of the fiber bundle, by $\theta_{max,th}=(d_1+d_2)/f_1$ to be 0.50 rad. Experiments using a standard scattering sample 122 indicate the usable angular range to be $\theta_{min}=0.12$ rad. to $\theta_{max}=0.45$ rad. $d_1$, for example, can be minimized by fabricating a channel in the distal ferrule 123 and positioning the delivery fiber 16" in the channel. The fiber bundle 116 is spatially coherent, resulting in a reproduction of the collected angular scattering distribution at the proximal face. Additionally, as all fibers in the bundle 116 are path length matched to within the coherence length, the optical path length traveled by scattered light 122 at each angle is identical. The system disclosed in "Fiber-optic-bundle-based optical coherence tomography," by T. Q. Xie, D. Mukai, S. G. Guo, M. Brenner, and Z. P. Chen in *Optics Letters* 30(14), 1803-1805 (2005) (hereinafter "Xie"), incorporated by reference herein in its entirety, discloses a multimode coherent fiber bundle into a time-domain optical coherence tomography system and demonstrated that the modes of light coupled into an individual fiber will travel different path lengths. In the example herein of the disclosed embodiments, it was experimentally determined that the higher order modes are offset from the fundamental mode by 3.75 mm, well beyond the depth (~100 μm) required for gathering clinically relevant data. Additionally, the power in the higher order modes had a minimal affect on dynamic range as the sample arm power is significantly less than the reference arm power. Finally, it should be noted that while the system disclosed in Xie collected data serially through individual fibers, the example of the disclosed embodiments herein uses 130 fibers to simultaneously collect scattered light across a range of angles in parallel, resulting in rapid data collection.

The angular distribution exiting a proximal end 124 of the fiber bundle 116 is relayed by the 4f imaging system of L2 and L3 ($f_2=3.0$ cm, $f_3=20.0$ cm) to the input slit 48" of the imaging spectrograph 29" (e.g. Acton Research, InSpectrum 150). The theoretical magnification of the 4f imaging system is ($f_3/f_2$) 6.67 in this example. Experimentally, the magnification was measured to be M=7.0 in this example with the discrepancy most likely due to the position of the proximal face 124 of the fiber bundle 116 with relation to lens L2 (126). The resulting relationship between vertical position on the spectrograph slit 48", y, and θ is $y=Mf_1(\theta-\theta_{min})$. The optical path length of the reference arm is matched to that of the fundamental mode of the sample arm. Light 127 exiting the reference fiber 14" is collimated by lens L4 (128) (e.g. f=3.5 cm, spot size=8.4 mm) to match the phase front curvature of the sample light and to produce even illumination across the slit 48" of the imaging spectrograph 29". A reference field 130 may be attenuated by a neutral density filter 132 and mixed with the angular scattering distribution at beamsplitter BS (134). The mixed fields 136 are dispersed with a high resolution grating (e.g. 1200 lines/mm) and detected using an integrated, cooled CCD (not shown) (e.g. 1024×252, 24 μm×24 μm pixels, 0.1 nm resolution) covering a spectral range of 99 nm centered at 840 nm, for example.

The detected signal 136, a function of wavelength, λ, and θ, can be related to the signal and reference fields ($E_s$, $E_r$) as:

$$I(\lambda_m, y_n) = \langle |E_r(\lambda_m, y_n)|^2 \rangle + \langle |E_S(\lambda_m, y_n)|^2 \rangle + 2\text{Re} \langle E_S(\lambda_m, y_n) E_r^*(\lambda_m, y_n) \rangle \cos\phi, \quad (1)$$

where φ is the phase difference between the two fields, (m,n) denotes a pixel on the CCD, and $\langle \ldots \rangle$ denotes a temporal average. $I(\lambda_m, \theta_n)$ is uploaded to a PC using LabVIEW manufactured by National Instruments software and processed in 320 ms to produce a depth and angle resolved contour plot of scattered intensity. The processing of the angle-resolved scattered field to obtain depth and size information described above, and in particular reference to the data acquisition apparatus of FIGS. 1A and 1B, can then used to obtain angle-resolved, depth-resolved information about the sample 18" using the scattered mixed field 136 generated by the apparatus in FIG. 8.

The embodiments set forth above represent the necessary information to enable those skilled in the art to practice the disclosed embodiments and illustrate the best mode of practicing the disclosed embodiments. Upon reading the following description in light if the accompanying drawings figures, those skilled in the art will understand the concepts of the disclosed embodiments and will recognize applications of these concepts not particularly addressed herein. It should be understood that these concepts and applications fall within the scope of the disclosure.

Those skilled in the art will recognize improvements and modifications to the preferred embodiments of the disclosed embodiments. All such improvements and modifications are considered within the scope of the concepts disclosed herein and the claims that follow.

We claim:

1. A method of obtaining depth-resolved spectra of a sample for determining characteristics within the sample, comprising:
    emitting a source beam onto a splitter, wherein the splitter splits light from the source beam to produce a reference beam and a sample beam;
    directing the sample beam towards the sample at an angle while maintaining an optical path length of the sample beam to the sample;
    receiving an angle-resolved scattered sample beam as a result of the sample beam scattering at a multitude of scattered angles off of the sample, wherein the angle-resolved scattered sample beam contains the angular scattering distribution of the scattered sample beam;
    cross-correlating the angle-resolved scattered sample beam with the reference beam to produce an angle-resolved cross-correlated signal about the sample;
    spectrally dispersing the angle-resolved cross-correlated signal to yield an angle-resolved, spectrally-resolved cross-correlation profile having depth-resolved information about the sample at the multitude of scattered angles; and
    processing the angle-resolved, spectrally-resolved cross-correlation profile to obtain depth-resolved information about the sample.

2. The method of claim 1, further comprising determining the depth of the scatterers of the sample at a multitude of different points on the sample from the angle-resolved, spectrally-resolved cross-correlation profile.

3. The method of claim 1, wherein processing the angle-resolved, spectrally-resolved cross-correlation profile comprises Fourier transforming the angle-resolved, spectrally-resolved cross-correlation profile to produce depth-resolved information about the sample.

4. The method of claim 1, further comprising recovering size information about the scatterers from the angle-resolved, spectrally-resolved cross-correlation profile.

5. The method of claim 4, wherein recovering the size information comprises comparing the angular scattering distribution of the angle-resolved, spectrally-resolved cross-correlation profile to a database of angular scattering distributions generated with a finite element method (FEM) or T-Matrix calculations.

6. The method of claim 4, wherein recovering the size information comprises comparing the angular scattering distribution of the angle-resolved, spectrally-resolved cross-correlation profile to a predicted analytically or numerically calculated angular scattering distribution of the sample.

7. The method of claim 6, wherein the predicted analytically or numerically calculated angular scattering distribution of the sample is a Mie theory angular scattering distribution of the sample.

8. The method of claim 6, further comprising filtering the angular scattering distribution of the sample before comparing the angular scattering distribution.

9. The method of claim 6, further comprising calculating a Gaussian distribution of sizes of the scatterers by calculating a mean diameter and a standard deviation to model the angular scattering distribution of the sample.

10. The method of claim 1, further comprising collimating the sample beam to produce a collimated sample beam, wherein directing the sample beam towards the sample at an angle comprises directing the collimated sample beam towards the sample at an angle.

11. The method of claim 1, further comprising collimating the reference beam to produce a collimated reference beam.

12. The method of claim 1, wherein the reference beam is reflected before the cross-correlating to create a reflected reference beam.

13. The method of claim 12, wherein the reflected reference beam is created by reflecting the reference beam off of a reference minor.

14. The method of claim 1, wherein cross-correlating the angle-resolved scattered sample beam with the reference beam comprises:
determining an interference term by measuring the intensity of the angle-resolved scattered sample beam and the reference beam independently; and
subtracting the interference term from the total intensity of the angle-resolved scattered sample beam.

15. The method of claim 1, further comprising maintaining an optical path length of the reference beam.

16. The method of claim 1, wherein spectrally dispersing the angle-resolved cross-correlated signal comprises directing the angle-resolved scattered sample beam which has been combined with the reference beam into a spectrograph.

17. The method of claim 16, wherein the spectrograph comprises an imaging spectrograph comprised of a plurality of imaging points wherein each of the plurality of imaging points corresponds to a specific scattering angle in order to produce the angle-resolved, spectrally-resolved cross-correlation profile about the sample.

18. The method of claim 16, wherein the spectrograph comprises a multi-channel spectrograph comprised of a plurality of channels, wherein each of the plurality of channels corresponds to a specific scattering angle in order to produce the angle-resolved, spectrally-resolved cross-correlation profile about the sample.

19. The method of claim 1, wherein receiving the angle-resolved scattered sample beam as a result of the sample beam scattering at the multitude of scattered angles off of the sample in parallel comprises capturing the angular distribution of the scattered sample beam at an end of a fiber bundle comprised of a plurality of fibers.

20. The method of claim 19, wherein the plurality of fibers in the fiber bundle are arranged to collect different angular scatterings of the scattered sample beam to collect the angular scattering distribution of the scattered sample beam.

21. The method of claim 19, wherein the fiber bundle comprises a linear array of single mode fibers.

22. The method of claim 19, further comprising carrying the sample beam on a delivery fiber wherein the delivery fiber delivers the sample beam at an oblique angle with respect to the sample and the fiber bundle so that a specular reflection due to the sample is not received by the fiber bundle.

23. The method of claim 19, further comprising receiving the angle-resolved scattered sample beam via a Fourier transform property of an optical element placed in between the fiber bundle and the sample to receive the angle-resolved scattered sample beam located at another focus of the optical element.

24. The method of claim 19, wherein the plurality of fibers possess the same or substantially the same spatial arrangement at distal and proximal ends of the plurality of fibers so that the fiber bundle is spatially coherent with respect to conveying the angular distribution of the angle-resolved scattered sample beam.

25. The method of claim 23, wherein the optical element is either a lens or an imaging optical element.

26. The method of claim 1, further comprising splitting more light at the splitter from the source beam to produce more light in the sample beam than in the reference beam.

27. The method of claim 1, further comprising varying an optical path length of the reference beam to align the optical path length of the reference beam to the optical path length of the sample beam.

28. An apparatus for obtaining depth-resolved spectra of a sample for determining characteristics within the sample, comprising:
a receiver configured to:
receive an angle-resolved scattered sample beam as a result of a sample beam, split by a splitter from a source beam, scattered at a multitude of scattered angles off of the sample, wherein the angle-resolved scattered sample beam contains the angular scattering distribution of the scattered sample beam while maintaining an optical path length of the sample beam to the sample;
receive a reference beam split by the splitter from the source beam; and
cross-correlate the angle-resolved scattered sample beam with the reference beam to produce an angle-resolved cross-correlated signal about the sample;
a detector configured to spectrally disperse the angle-resolved cross-correlated signal to yield an angle-resolved, spectrally-resolved cross-correlation profile having depth-resolved information about the sample at the multitude of scattered angles; and
a processor configured to receive the angle-resolved, spectrally-resolved cross-correlation profile.

29. The apparatus of claim 28, wherein the processor is configured to determine the depth of the scatterers of the sample at a multitude of different points on the sample from the angle-resolved, spectrally-resolved cross-correlation profile.

30. The apparatus of claim 28, wherein the processor is further configured to Fourier transform the angle-resolved, spectrally-resolved cross-correlation profile to produce depth-resolved information about the sample as a function of angle and depth.

31. The apparatus of claim 28, wherein the processor is further configured to recover size information about the scatterers from the angle-resolved, spectrally-resolved cross-correlation profile.

32. The apparatus of claim 31, wherein the processor recovers the size information by comparing the angular scattering distribution of the sample to a predicted analytically or numerically calculated angular scattering distribution of the sample.

33. The apparatus of claim 32, wherein the predicted analytically or numerically calculated angular scattering distribution of the sample is a Mie theory angular scattering distribution of the sample.

34. The apparatus of claim 32, wherein the processor is further configured to filter the angular scattering distribution of the sample before comparing the angular scattering distribution of the sample to a predicted analytically or numerically calculated angular scattering distribution of the sample.

35. The apparatus of claim 34, wherein the processor is further configured to identify a Gaussian distribution of sizes of the scatterers by identifying a mean diameter and a standard deviation to model the angular scattering distribution.

36. The apparatus of claim 28, wherein the sample beam is collimated.

37. The apparatus of claim 28, wherein the reference beam is collimated.

38. The apparatus of claim 28, further comprising a reflection device configured to receive and reflect the reference beam wherein the receiver receives the reflected reference beam.

39. The apparatus of claim 38, wherein the reflection device is a reference mirror.

40. The apparatus of claim 28, wherein the splitter is an optical fiber splitter.

41. The apparatus of claim 28, wherein the source beam is comprised of a light selected from the group consisting of a white light from an arc lamp, a thermal source, a light-emitting diode (LED), a coherent light from a broadband laser, a superluminescent diode, a diode laser, and a supercontinuum source.

42. The apparatus of claim 28, wherein the splitter is attached to a reference arm.

43. The apparatus of claim 28, wherein the sample is attached to a sample arm.

44. The apparatus of claim 28, wherein the detector comprises a spectrograph.

45. The apparatus of claim 28, wherein the receiver is a fiber bundle comprised of a plurality of fibers.

46. The apparatus of claim 45, wherein the plurality of fibers in the fiber bundle are arranged to collect different angular scatterings of the scattered sample beam to collect the angular scattering distribution of the angle-resolved scattered sample beam.

47. The apparatus of claim 46, wherein the fiber bundle comprises a linear array of single mode fibers.

48. The apparatus of claim 46, further comprising a delivery fiber that carries the sample beam so that the delivery fiber delivers the sample beam at an oblique angle with respect to the sample and the fiber bundle so that a specular reflection due to the sample is not received by the fiber bundle.

49. The apparatus of claim 46, wherein the plurality of fibers is positioned at one focus of an optical element to receive the angle-resolved scattered sample beam which is located at another focus of the optical element such that the fiber bundle receives the angular scattering distribution of scattered light via a Fourier transform property of the optical element.

50. The apparatus of claim 49, wherein the optical element is either a lens or an imaging optical element.

51. The apparatus of claim 46, wherein the plurality of fibers possess the same or substantially the same spatial arrangement at distal and proximal ends of the plurality of fibers so that the fiber bundle is spatially coherent with respect to conveying the angular scattering distribution of the angle-resolved scattered sample beam.

52. The apparatus of claim 28, wherein the splitter splits more light from the source beam to produce the sample beam than to produce the reference beam.

53. An apparatus for obtaining depth-resolved spectra of a sample for determining characteristics within the sample, comprising:
at least one delivery fiber that carries a sample beam wherein the sample beam is directed to the sample over the at least one delivery fiber while maintaining an optical path length of the sample beam to the sample and scattered at a multitude of angles off of the sample to produce a scattered sample beam;
a fiber-optic receiver comprised of a plurality of fibers configured to receive the scattered sample beam from the sample, such that the fiber-optic receiver receives an angular scattering distribution of the scattered sample beam;
a beam splitter configured to cross-correlate the angular scattering distribution of the scattered sample beam with a reference beam to produce an angle-resolved cross-correlated signal about the sample;
a detector that spectrally disperses the angle-resolved cross-correlated signal to yield an angle-resolved, spectrally-resolved cross-correlation profile at each of the multitude of angles; and
a processor configured to receive and analyze the angle-resolved, spectrally-resolved cross-correlation profile.

54. The apparatus of claim 53, wherein the processor is further configured to obtain depth-resolved information about the sample from the angle-resolved, spectrally-resolved cross-correlation profile.

55. The apparatus of claim 53, wherein the processor is further configured to process the angle-resolved cross-correlated signal to obtain depth-resolved information about the scatterers of the sample at a multitude of different points on the sample from the angle-resolved, spectrally-resolved cross-correlation profile.

56. The apparatus of claim 53, wherein the processor is further configured to recover size information about the scatterers from the angle-resolved, spectrally-resolved cross-correlation profile.

57. The apparatus of claim 53, wherein the plurality of fibers in the fiber-optic receiver are arranged to collect different angular scatterings of the sample beam to collect the angular scattering distribution of the scattered sample beam.

58. The apparatus of claim 53, wherein the fiber-optic receiver comprises a linear array of single mode fibers.

59. The apparatus of claim 53, wherein the plurality of fibers possess the same spatial arrangement at distal and proximal ends of the plurality of fibers so that the fiber-optic receiver is spatially coherent with respect to conveying the angular scattering distribution of the scattered sample beam.

60. The apparatus of claim 53, wherein the plurality of fibers is positioned at one focus of an optical element to receive the scattered sample beam which is located at another focus of the optical element such that the fiber-optic receiver receives the angular scattering distribution of scattered light.

61. The apparatus of claim 60, wherein the fiber-optic receiver receives the angular scattering distribution of scattered light via a Fourier transform property of the optical element.

62. The apparatus of claim 60, wherein the optical element is either a lens or an imaging optical element.

63. The apparatus of claim 53, wherein the processor is further configured to Fourier transform the angled-resolved, spectrally-resolved cross-correlation profile to produce depth-resolved information about the sample as a function of angle and depth.

64. The apparatus of claim 53, wherein a distal end of the fiber-optic receiver is located in a conjugate Fourier transform plane of the sample.

65. The apparatus of claim 53, wherein the reference beam is collimated to overlap with the scattered sample beam from the sample.

66. The apparatus of claim 53, wherein the fiber-optic receiver is comprised of a fiber-optic bundle.

\* \* \* \* \*